US009623255B2

(12) United States Patent
Libbus

(10) Patent No.: US 9,623,255 B2
(45) Date of Patent: Apr. 18, 2017

(54) INTERMITTENT NEURAL STIMULATION WITH PHYSIOLOGIC RESPONSE MONITOR

(71) Applicant: Cardiac Pacemakers, Inc., St. Paul, MN (US)

(72) Inventor: Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 400 days.

(21) Appl. No.: 14/218,092

(22) Filed: Mar. 18, 2014

(65) Prior Publication Data

US 2014/0200634 A1    Jul. 17, 2014

Related U.S. Application Data

(60) Continuation of application No. 13/396,405, filed on Feb. 14, 2012, now Pat. No. 8,682,434, which is a
(Continued)

(51) Int. Cl.
*A61N 1/32* (2006.01)
*A61N 1/372* (2006.01)
*A61N 1/36* (2006.01)

(52) U.S. Cl.
CPC ...... *A61N 1/37264* (2013.01); *A61N 1/36114* (2013.01); *A61N 1/36117* (2013.01)

(58) Field of Classification Search
CPC ............ A61N 1/36114; A61N 1/36117; A61N 1/36139; A61N 1/36135; A61N 1/36167;
(Continued)

(56) References Cited

U.S. PATENT DOCUMENTS 4,161,945 A   7/1979 Grossman
4,251,118 A   2/1981 Rothen et al.
(Continued)

FOREIGN PATENT DOCUMENTS

JP    2004526471 A   9/2004
JP     201220185 A   2/2012
(Continued)

OTHER PUBLICATIONS

"U.S. Appl. No. 11/000,249, Advisory Action mailed Jan. 26, 2011", 3 pgs.
(Continued)

*Primary Examiner* — Michael Kahelin
*Assistant Examiner* — Minh Duc Pham
(74) *Attorney, Agent, or Firm* — Schwegman Lundberg & Woessner, P.A.

(57) ABSTRACT

Various aspects of the present subject matter provide an implantable medical device. In various embodiments, the device comprises a pulse generator, a first monitor and a controller. The pulse generator is adapted to generate a neural stimulation signal for a neural stimulation therapy. The neural stimulation signal has at least one adjustable parameter. The first monitor is adapted to detect an undesired effect. In some embodiments, the undesired effect is myocardial infarction. The controller is adapted to respond to the first monitor and automatically adjust the at least one adjustable parameter of the neural stimulation signal to avoid the undesired effect of the neural stimulation therapy. Other aspects are provided herein.

20 Claims, 13 Drawing Sheets

Related U.S. Application Data division of application No. 11/000,249, filed on Nov. 30, 2004, now Pat. No. 8,126,559.

(58) Field of Classification Search
CPC ............ A61N 1/36146; A61N 1/36067; A61N 1/37247; A61N 1/37264
USPC .......................................................... 607/9
See application file for complete search history.

(56) References Cited

U.S. PATENT DOCUMENTS

| | | | |
|---|---|---|---|
| 4,436,093 A | 3/1984 | Belt | |
| 4,627,441 A | 12/1986 | Martin | |
| 4,646,258 A | 2/1987 | Miodownik | |
| 4,791,931 A | 12/1988 | Slate | |
| 5,111,815 A | 5/1992 | Mower | |
| 5,199,428 A * | 4/1993 | Obel | A61N 1/36557 600/516 |
| 5,203,326 A | 4/1993 | Collins | |
| 5,243,980 A | 9/1993 | Mehra | |
| 5,318,592 A | 6/1994 | Schaldach | |
| 5,330,507 A | 7/1994 | Schwartz | |
| 5,356,425 A | 10/1994 | Bardy et al. | |
| 5,374,282 A | 12/1994 | Nichols et al. | |
| 5,411,531 A | 5/1995 | Hill et al. | |
| 5,522,854 A | 6/1996 | Ideker et al. | |
| 5,549,649 A | 8/1996 | Florio et al. | |
| 5,658,318 A | 8/1997 | Stroetmann et al. | |
| 5,690,681 A | 11/1997 | Geddes et al. | |
| 5,700,282 A | 12/1997 | Zabara | |
| 5,916,239 A | 6/1999 | Geddes et al. | |
| 6,006,134 A | 12/1999 | Hill et al. | |
| 6,058,331 A | 5/2000 | King | |
| 6,073,048 A | 6/2000 | Kieval et al. | |
| 6,169,918 B1 | 1/2001 | Haefner et al. | |
| 6,181,966 B1 | 1/2001 | Nigam | |
| 6,341,236 B1 | 1/2002 | Osorio et al. | |
| 6,493,585 B2 | 12/2002 | Plicchi et al. | |
| 6,511,500 B1 | 1/2003 | Rahme | |
| 6,522,926 B1 | 2/2003 | Kieval et al. | |
| 6,622,041 B2 | 9/2003 | Terry, Jr. et al. | |
| 6,628,987 B1 | 9/2003 | Hill et al. | |
| 6,928,320 B2 | 8/2005 | King | |
| 7,123,961 B1 * | 10/2006 | Kroll | A61N 1/36114 607/2 |
| 7,123,967 B2 | 10/2006 | Weinberg | |
| 7,260,431 B2 | 8/2007 | Libbus et al. | |
| 7,321,793 B2 | 1/2008 | Ben Ezra et al. | |
| 7,460,906 B2 | 12/2008 | Libbus | |
| 7,486,991 B2 | 2/2009 | Libbus et al. | |
| 7,551,958 B2 | 6/2009 | Libbus et al. | |
| 7,643,875 B2 | 1/2010 | Hiel, Jr. et al. | |
| 7,647,114 B2 | 1/2010 | Libbus | |
| 7,657,312 B2 | 2/2010 | Pastore et al. | |
| 7,706,884 B2 | 4/2010 | Libbus | |
| 7,769,450 B2 | 8/2010 | Libbus et al. | |
| 7,778,703 B2 * | 8/2010 | Gross | A61N 1/0551 607/118 |
| 7,783,353 B2 | 8/2010 | Libbus et al. | |
| 7,869,881 B2 | 1/2011 | Libbus et al. | |
| 8,285,389 B2 | 10/2012 | Libbus et al. | |
| 8,442,640 B2 | 5/2013 | Libbus | |
| 8,682,434 B2 | 3/2014 | Libbus | |
| 2002/0068875 A1 | 6/2002 | Schroeppel et al. | |
| 2002/0072776 A1 | 6/2002 | Osorio et al. | |
| 2002/0107553 A1 | 8/2002 | Hill et al. | |
| 2002/0165586 A1 | 11/2002 | Hill et al. | |
| 2003/0004549 A1 | 1/2003 | Hill et al. | |
| 2003/0040774 A1 | 2/2003 | Terry, Jr. et al. | |
| 2003/0045909 A1 | 3/2003 | Gross et al. | |
| 2003/0060848 A1 | 3/2003 | Keival et al. | |
| 2003/0060858 A1 | 3/2003 | Kieval et al. | |
| 2003/0065365 A1 | 4/2003 | Zhu et al. | |
| 2003/0078623 A1 | 4/2003 | Weinberg et al. | |
| 2003/0212445 A1 | 11/2003 | Weinberg | |
| 2004/0044377 A1 | 3/2004 | Larsson | |
| 2004/0138721 A1 | 7/2004 | Osorio et al. | |
| 2005/0143779 A1 | 6/2005 | Libbus | |
| 2005/0143785 A1 | 6/2005 | Libbus | |
| 2005/0149126 A1 | 7/2005 | Libbus | |
| 2005/0149127 A1 | 7/2005 | Libbus | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0187584 A1 | 8/2005 | Denker et al. | |
| 2006/0079945 A1 | 4/2006 | Libbus | |
| 2006/0095080 A1 | 5/2006 | Libbus et al. | |
| 2006/0106429 A1 | 5/2006 | Libbus et al. | |
| 2006/0224188 A1 | 10/2006 | Libbus et al. | |
| 2006/0271108 A1 | 11/2006 | Libbus et al. | |
| 2007/0021792 A1 | 1/2007 | Kieval et al. | |
| 2007/0142864 A1 | 6/2007 | Libbus et al. | |
| 2007/0142871 A1 | 6/2007 | Libbus et al. | |
| 2008/0015657 A1 | 1/2008 | Haefner | |
| 2008/0021507 A1 | 1/2008 | Libbus et al. | |
| 2008/0167694 A1 | 7/2008 | Bolea et al. | |
| 2010/0010553 A1 | 1/2010 | Libbus et al. | |
| 2010/0106226 A1 | 4/2010 | Libbus | |
| 2010/0121399 A1 | 5/2010 | McCabe et al. | |
| 2010/0274321 A1 | 10/2010 | Libbus | |
| 2010/0286740 A1 | 11/2010 | Libbus et al. | |
| 2011/0082514 A1 | 4/2011 | Libbus et al. | |
| 2012/0143275 A1 | 6/2012 | Libbus | |
| 2013/0231717 A1 | 9/2013 | Libbus | |

FOREIGN PATENT DOCUMENTS

| | | |
|---|---|---|
| JP | 2012236083 A | 12/2012 |
| WO | WO-0226318 A1 | 4/2002 |
| WO | WO-03011388 A2 | 2/2003 |
| WO | WO-2005113066 A1 | 12/2005 |
| WO | WO-2006031331 A1 | 3/2006 |
| WO | WO-2006098996 A1 | 9/2006 |
| WO | WO-2006121929 A1 | 11/2006 |
| WO | WO-2007078410 A1 | 7/2007 |
| WO | WO-2008063396 A1 | 5/2008 |

OTHER PUBLICATIONS

"U.S. Appl. No. 11/000,249, Examiner Interview Summary mailed Aug. 27, 2010", 3 pgs.
"U.S. Appl. No. 11/000,249, Final Office Action mailed Jan. 14, 2010", 10 pgs.
"U.S. Appl. No. 11/000,249, Final Office Action mailed Sep. 23, 2008", 9 pgs.
"U.S. Appl. No. 11/000,249, Final Office Action mailed Oct. 13, 2010", 12 pgs.
"U.S. Appl. No. 11/000,249, Non Final Office Action mailed Apr. 13, 2011", 9 pgs.
"U.S. Appl. No. 11/000,249, Non-Final Office Action mailed Jan. 24, 2008", 11 pgs.
"U.S. Appl. No. 11/000,249, Non-Final Office Action mailed Apr. 26, 2010", 7 pgs.
"U.S. Appl. No. 11/000,249, Non-Final Office Action mailed Jul. 15, 2009", 9 pgs.
"U.S. Appl. No. 11/000,249, Notice of Allowance mailed Oct. 28, 2011", 7 pgs.
"U.S. Appl. No. 11/000,249, Response filed Jan. 13, 2011 to Final Office Action mailed Oct. 13, 2010", 19 pgs.
"U.S. Appl. No. 11/000,249, Response filed Feb. 23, 2009 to Final Office Action mailed Sep. 23, 2008", 13 pgs.
"U.S. Appl. No. 11/000,249, Response filed Apr. 14, 2010 to Final Office Action mailed Jan. 14, 2010", 14 pgs.
"U.S. Appl. No. 11/000,249, Response filed Apr. 16, 2009 to Restriction Requirement mailed Mar. 30, 2009", 11 pgs.
"U.S. Appl. No. 11/000,249, Response filed Apr. 29, 2008 to

(56) References Cited

OTHER PUBLICATIONS

Non-Final Office Action mailed Jan. 24, 2008", 16 pgs.

"U.S. Appl. No. 11/000,249, Response filed Aug. 26, 2010 to Non Final Office Action mailed Apr. 26, 2010", 15 pgs.

"U.S. Appl. No. 11/000,249, Response filed Oct. 13, 2011 to Non Final Office Action mailed Apr. 13, 2011", 16 pgs.

"U.S. Appl. No. 11/000,249, Response filed Oct. 15, 2009 to Non Final Office Action mailed Jul. 15, 2009", 15 pgs.

"U.S. Appl. No. 11/000,249, Response filed Nov. 2, 2007 to Restriction Requirement mailed Oct. 2, 2007", 11 pgs.

"U.S. Appl. No. 11/000,249, Restriction Requirement mailed Mar. 30, 2009", 5 pgs.

"U.S. Appl. No. 11/000,249, Restriction Requirement mailed Oct. 2, 2007", 5 pgs.

"U.S. Appl. No. 13/396,405, Response filed Aug. 27, 2013 to Final Office Action mailed Jul. 9, 2013", 17 pgs.

"U.S. Appl. No. 13/396,405, Final Office Action mailed Jul. 9, 2013", 14 pgs.

"U.S. Appl. No. 13/396,405, Non Final Office Action mailed Aug. 21, 2012", 13 pgs.

"U.S. Appl. No. 13/396,405, Notice of Allowance mailed Nov. 8, 2013", 10 pgs.

"U.S. Appl. No. 13/396,405, Response filed Nov. 20, 2012 to Non Final Office Action mailed Aug. 21, 2012", 12 pgs.

Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.

Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.

Schauerte, P, et al., "Ventricular rate control during atrial fibrillation by cardiac parasympathetic nerve stimulation: a transvenous approach", J Am Coll Cardiol., 34(7), (Dec. 1999), 2043-50.

"U.S. Appl. No. 10/939,544, Examiner Interview Summary mailed Sep. 3, 2008", 14 pgs.

"U.S. Appl. No. 10/939,544, Examiner Interview Summary mailed Nov. 6, 2006", 2 pgs.

"U.S. Appl. No. 10/939,544, Final Office Action mailed Mar. 5, 2009", 14 pgs.

"U.S. Appl. No. 10/939,544, Notice of Allowance mailed Sep. 3, 2009", 12 pgs.

"U.S. Appl. No. 10/939,544, Response filed Aug. 5, 2009 to Final Office Action mailed Mar. 5, 2009", 16 pgs.

"U.S. Appl. No. 11/428,131, Substitute Preliminary Statement dated Jul. 5, 2006", 2 pgs.

"U.S. Appl. No. 11/558,083, Non-Final Office Action mailed Jun. 26, 2009", 17 pgs.

"U.S. Appl. No. 11/558,083, Notice of Allowance mailed Apr. 8, 2010", 7 pgs.

"U.S. Appl. No. 11/558,083, Preliminary Amendment mailed Nov. 13, 2006", 3 pgs.

"U.S. Appl. No. 11/558,083, Response filed Dec. 22, 2009 to Non-Final Office Action mailed Jun. 26, 2009", 15 pgs.

"U.S. Appl. No. 12/651,515, Notice of Allowance mailed Jan. 18, 2013", 5 pgs.

"U.S. Appl. No. 12/651,515, Response filed Dec. 4, 2012 to Non Final Office Action mailed Sep. 4, 2012", 9 pgs.

"U.S. Appl. No. 12/840,981, Ex Parte Quayle Action mailed Mar. 5, 2012", 7 pgs.

"U.S. Appl. No. 12/968,797, Non Final Office Action mailed Oct. 3, 2013", 6 pgs.

"U.S. Appl. No. 13/868,287, Non Final Office Action mailed Oct. 23, 2013", 7 pgs.

"European Application Serial No. 05787559.3, Response filed Jul. 23, 2009 to Communication mailed Jan. 29, 2009", 12 pgs.

"Japanese Application Serial No. 2007-531174, Office Action Response mailed Oct. 28, 2011", with English Amended Claims, 8 pgs.

"Japanese Application Serial No. 2012-197413, Office Action mailed Oct. 2, 2013", With English Translation, 5 pgs.

Chapleau, M. W., et al., "Contrasting effects of static and pulsatile pressure on carotid baroreceptor activity in dogs", Circulation, vol. 61, No. 5, (Nov. 1987), 648-658.

Li, M., et al., "Vagal nerve stimulation markedly improves long-term survival after chronic heart failure in rats", Circulation, 109(1), (2004), 120-124.

Libbus, I., et al., "Hypertension Therapy Based on Activity and Circadian Rhythm", U.S. Appl. No. 12/968,797, filed Dec. 15, 2010, 75 pgs.

Libbus, I., et al., "Neural Stimulation Modulation Based on Monitored Cardiovasular Parameter", U.S. Appl. No. 12/651,515, filed Jan. 4, 2010, 73 pgs.

Libbus, Imad, "Cardiac Rhythm Management Device With Neural Sensor", U.S. Appl. No. 10/992,320, filed Nov. 18, 2004, 65 pgs.

Libbus, Imad, "Neural Stimulation With Avoidance of Inappropriate Stimulation", U.S. Appl. No. 11/000,249, filed Nov. 30, 2004, 45 pgs.

Libbus, Imad, et al., "Sensing With Compensation for Neural Stimulator", U.S. Appl. No. 11/621,194, filed Jan. 9, 2007, 69 pgs.

Libbus, Imad, "Stimulator for Auricular Branch of Vagus Nerve", U.S. Appl. No. 11/005,703, filed Dec. 7, 2004, 35 pgs.

Libbus, Imad, "System and Method for Sustained Baroreflex Stimulation", U.S. Appl. No. 10/962,845, filed Oct. 12, 2004, 50 pgs.

Libbus, Imad, "System to Provide Myocardial and Neural Stimulation", U.S. Appl. No. 11/087,935, filed Mar. 23, 2005, 52 pgs.

* cited by examiner

US 9,623,255 B2

INTERMITTENT NEURAL STIMULATION WITH PHYSIOLOGIC RESPONSE MONITOR

CLAIM OF PRIORITY

This application is a continuation of and claims the benefit of priority under 35 U.S.C. §120 to U.S. patent application Ser. No. 13/396,405, filed on Feb. 14, 2012, now issued as U.S. Pat. No. 8,682,434, which is a division of and claims the benefit of priority under 35 U.S.C. §120 to U.S. patent application Ser. No. 11/000,249, filed on Nov. 30, 2004, now issued as U.S. Pat. No. 8,126,559, each of which is hereby incorporated by reference herein in its entirety.

CROSS REFERENCE TO RELATED APPLICATIONS

The following commonly assigned U.S. patent application is related, and is incorporated by reference herein in its entirety: "Sensing With Compensation for Neural Stimulator," U.S. patent application Ser. No. 10/746,847, filed on Dec. 24, 2003; and "System and Method for Filtering Neural Stimulation," U.S. patent application Ser. No. 10/982,001, filed Nov. 4, 2004, now issued as U.S. Pat. No. 8,200,331.

TECHNICAL FIELD

This application relates generally to neural stimulation and, more particularly, to systems, devices and methods to automatically avoid or prevent inappropriate neural stimulation.

BACKGROUND

Centrally mediated reflex pathways modulate cardiac rate, contractility, and excitability. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release.

Some neural stimulators treat a variety of disorders, such as epilepsy, obesity, and breathing disorders. Modulation of the sympathetic and parasympathetic nervous system with neural stimulation has been shown to have positive clinical benefits, such as protecting the myocardium from further remodeling and predisposition to fatal arrhythmias following a myocardial infarction. Experimentally, neural stimulation has been shown to have a significant effect on several cardiovascular conditions, and may be used to treat hypertension, post-MI remodeling, and heart failure.

However, neural stimulation may have undesired results. For example, neural stimulation in the vicinity of the heart may inadvertently stimulate the myocardium, altering intrinsic rate and activation sequence. That is, neural stimulation in the vicinity of the heart may have sufficient voltage and pulse width to capture the surrounding myocardium, resulting in unintended atrial or ventricular depolarization. Other potential undesired results include inappropriate stimulation of other nerves than the target nerve, and inappropriate stimulation of smooth muscle proximate to the target nerve.

SUMMARY

Various embodiments provide an implantable medical device, comprising a pulse generator, a first monitor and a controller. The pulse generator is adapted to generate a neural stimulation signal for a neural stimulation therapy. The neural stimulation signal has at least one adjustable parameter. The first monitor is adapted to detect an undesired effect. The controller is adapted to respond to the first monitor and automatically adjust the at least one adjustable parameter of the neural stimulation signal to avoid the undesired effect of the neural stimulation therapy.

Various embodiments provide an implantable device, comprising a neural stimulator, a first monitor, a second monitor, and a controller. The neural stimulator includes a pulse generator to generate a neural stimulation signal for a neural stimulation therapy, and a modulator to adjust at least one stimulation parameter of the neural stimulation signal. The first monitor is adapted to monitor at least one feedback parameter and provide a first signal indicative of the parameter during the neural stimulation therapy and a second signal indicative of the feedback parameter without the neural stimulation. The second monitor is adapted to monitor myocardial capture from the neural stimulation therapy and provide a third signal indicative of a detected myocardial capture. The controller is adapted to respond to the first, second and third signals, determine a detected change for the at least one stimulation parameter based on the first and second signals, and provide a therapy control signal to the modulator based on the third signal and the detected change to achieve a desired change for the at least one stimulation parameter while avoiding myocardial capture.

Various embodiments provide a method, comprising applying neural stimulation therapy to at least one targeted nerve, including generating a neural stimulation signal for use to provide the neural stimulation therapy, and further comprising monitoring a patient for an undesired response to the neural stimulation signal, and automatically adjusting at least one parameter of the neural stimulation signal to avoid the undesired response to the neural stimulation signal.

Various embodiments provide a method, comprising applying neural stimulation therapy to at least one targeted nerve, including generating a neural stimulation signal for use to provide the neural stimulation therapy, and further comprising monitoring a patient for both a desired response and an undesired response to the neural stimulation signal, and automatically adjusting at least one parameter of the neural stimulation signal to achieve the desired response and avoid the undesired response to the neural stimulation signal.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1B:
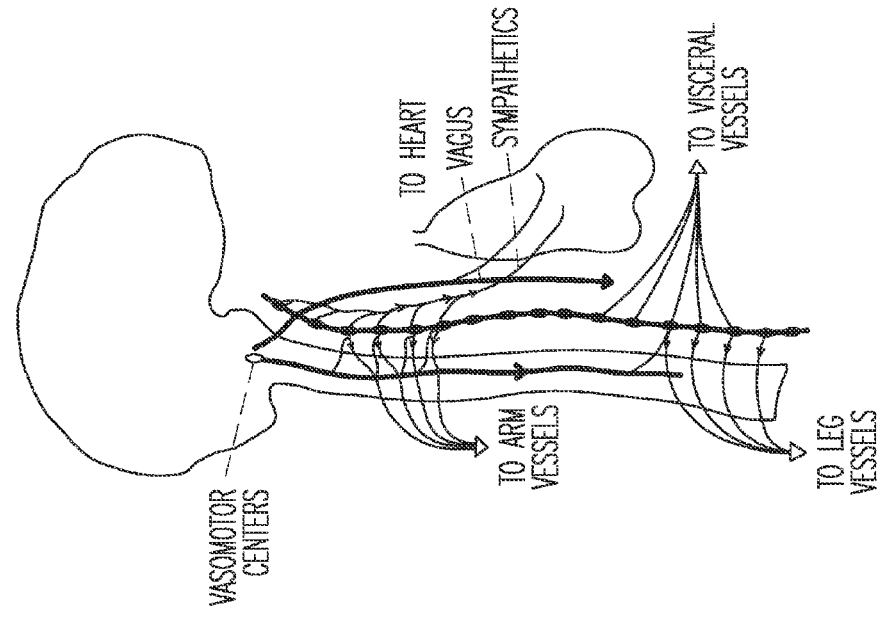
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This disclosure describes a neural stimulation device with the ability to detect undesired results of neural stimulation, such as the stimulation of an unintended region, and adjust neural stimulation parameters to avoid the undesired results. Some device embodiments stimulate a target nerve or nerves and avoid inappropriate stimulation and capture of the myocardia; some device embodiments stimulate a target nerve or nerves, and avoid inappropriate stimulation of smooth muscle proximate to the target nerve(s); and some device embodiments stimulate a target nerve or nerves, and avoid inappropriate stimulation of other nerves proximate to the target nerve(s).

Examples of inappropriate stimulation of a smooth muscle include stimulating a pectoral muscle and stimulating a diaphragm, which can cause undesired contractions or twitching in these muscles. Examples of inappropriate stimulation of other nerves include stimulation of laryngeal nerve, resulting in undesired coughing, and stimulation of the phrenic nerve, resulting in undesired hiccups, when the desired stimulation targets an afferent nerve such as the vagus nerve to stimulate the parasympathetic response.

A problem is neural stimulation in the vicinity of the heart (e.g. fat pads, great vessels, etc.) may have sufficient voltage/pulse width to capture the myocardium, and elicit atrial or ventricular depolarization. A solution is to apply an autocapture algorithm in the neural stimulation lead or other sensing leads to verify the absence of capture. If no capture, the stimulation is okay. If there is capture, the neural stimulation is adjusted to avoid capture. Some device embodiments to avoid inappropriate myocardial capture are able to detect myocardial activation, and automatically adjust stimulation above the nerve activation threshold and below the myocardial activation threshold. In various embodiments, the device monitors changes in physiological parameters to verify the presence of appropriate stimulation of the target nerve(s). Thus, the device adjusts neural stimulation parameters such as amplitude, frequency, etc. to insure neural activation and prevent myocardial activation.

A neural stimulation lead is placed in an appropriate location to provide neural stimulation therapy. For example, various embodiments provide an expandable stimulation lead placed in the pulmonary artery in the proximity of a high concentration of baroreceptors. Various embodiments provide a transvascular lead placed proximal to one of the cardiac fat pads, various embodiments provide an epicardial lead placed in the cardiac fat pad, various embodiments provide a cuff electrode placed around a nerve trunk, such as the aortic nerve, carotid nerve, or vagus nerve, and various embodiments provide a transvascular lead placed proximal to a nerve trunk.

A neural stimulation lead is connected to an implantable pulse generator, which delivers intermittent neural stimulation therapy through the lead to target nerve(s). Some device embodiments detect the presence of an inappropriate stimulation, such as myocardial activation, after each stimulation burst. In neural stimulation devices to avoid myocardial capture, some device embodiments detect electrical activity at the neural stimulation lead after a blanking period; and some device embodiments detect electrical activity at one or more distal leads, finding myocardial activation if sufficiently high electrical activity is sensed at the neural stimulation lead as compared to the distal lead. If the neural stimulation burst is too long and depolarization is masked by the stimulation burst, some device embodiments periodically test for myocardial activation using a short burst of neural stimulation to allow the device to accurately perform the detection algorithm.

If myocardial activation is detected, the neural stimulation device gradually reduces the intensity of neural stimulation by appropriately adjusting one or more parameters of the neural stimulation signal. Examples of adjustable parameters include but are not limited to amplitude, frequency, and pulse width. Detection and adjustment is repeated until the absence of myocardial activation is verified. In various embodiments, the device confirms the presence of neural stimulation after the absence of myocardial activation is confirmed. In some embodiments, the device monitors one or more physiological parameters such as heart rate, blood pressure and the like, immediately before and either during or immediately after a period of neural stimulation. Neural activation is detected if the physiological parameters are affected by a sufficient percentage in the expected direction. Some embodiments use the neural stimulation lead to record neural activity before and after a period of neural stimulation, and detect the presence of neural activation based on the response of the nerve traffic.

Various embodiments provide a programmable neurostimulation device with auto-threshold auto-capture features. In some device embodiments, the functional effect of the neurostimulation is programmed, and the device is adapted to automatically adjust stimulation parameters to achieve the programmed function while avoiding unwanted side effects like myocardial stimulation, neural stimulation of non-targeted nerves, and smooth muscle stimulation. An example of a programmed function effect of neural stimulation is to change a heart rate by a quantitative number or a percentage.

Provided below is a discussion of the autonomic nervous system, embodiments of systems/devices to provide neural stimulation with avoidance of inappropriate stimulation or undesired results, and embodiments of programmed therapy applications capable of being provided by the illustrated systems.

Autonomic Nervous System (ANS)

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Some neural stimulation affects the heart rate, blood pressure, vasodilation and vasoconstriction. The heart rate and force is increased when the sympathetic nervous system is stimulated, and is decreased when the sympathetic nervous system is inhibited (the parasympathetic nervous system is stimulated).

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells, such as within a cardiac fat pad, can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Figure 1A:
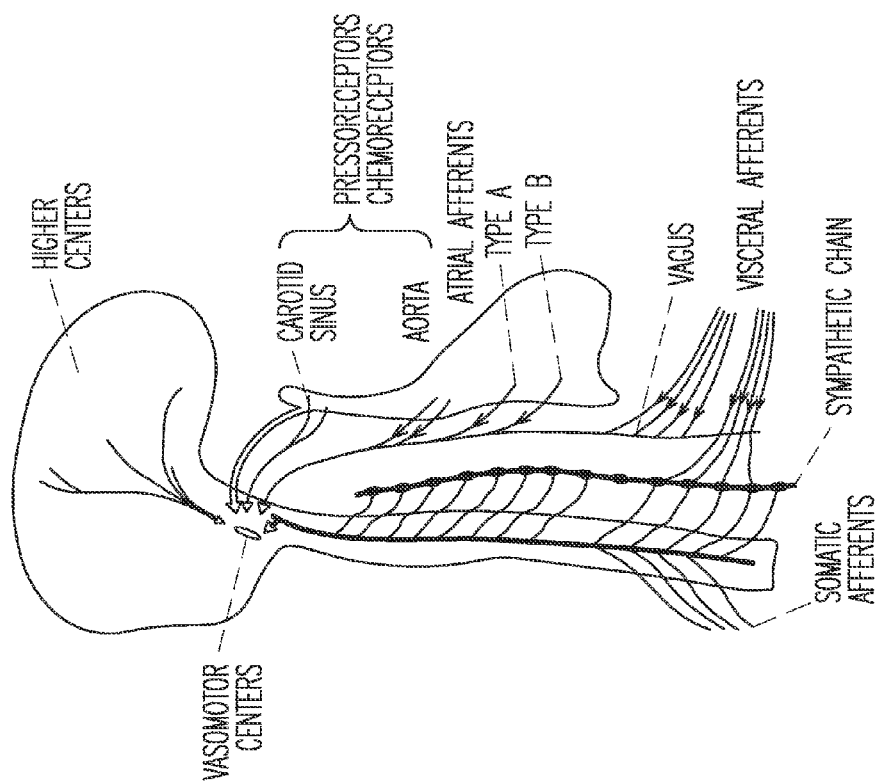

Baroreflex functions as a negative feedback system, and relates to a reflex mechanism triggered by stimulation of a baroreceptor or some afferent nerves. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. Additionally, neural stimulation of a non-targeted nerve along with a targeted nerve can also result in undesired responses.

Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figures 2A, 2B:
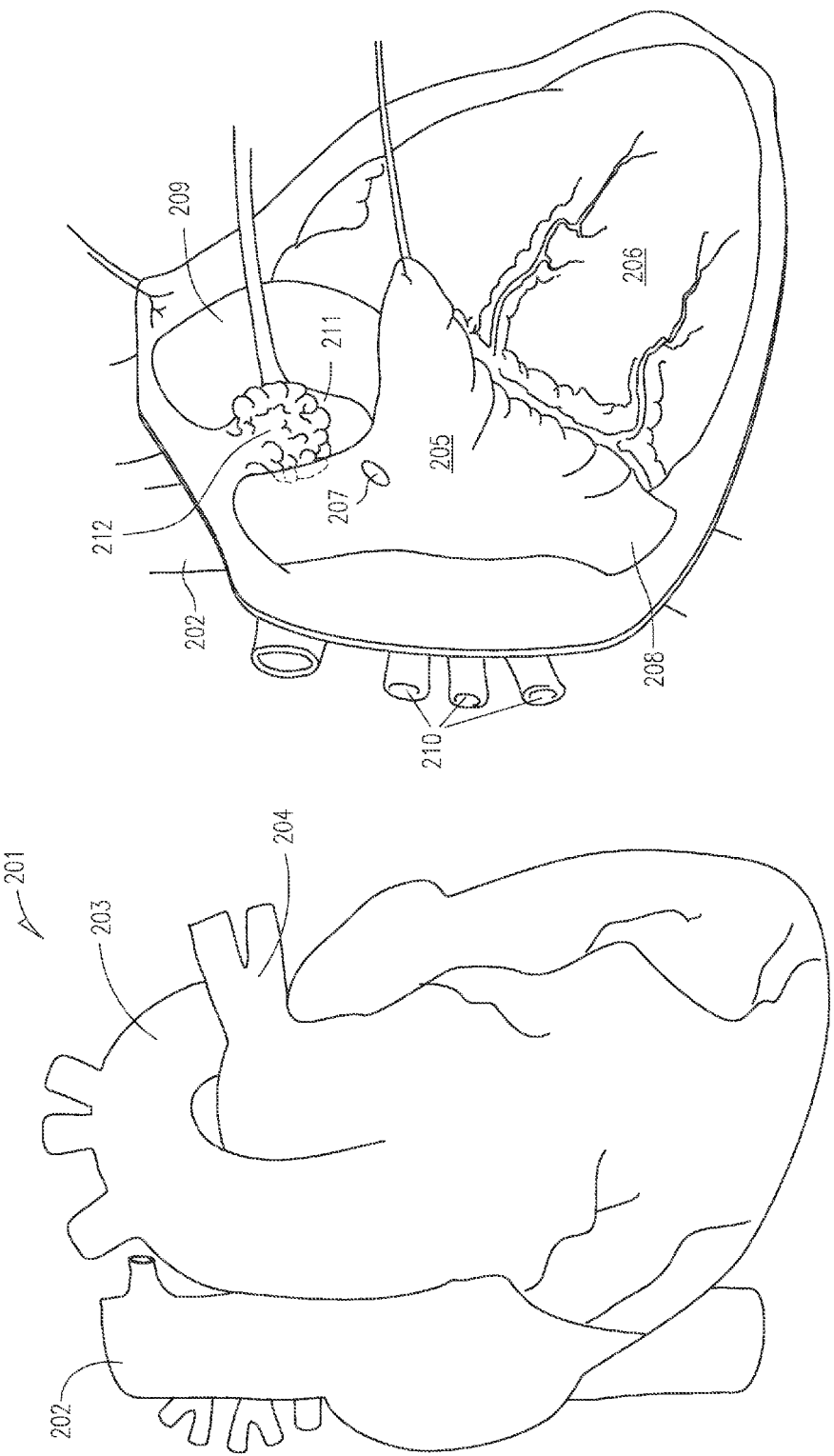
FIGS. 2A-2C illustrate a heart.
Figure 2C:
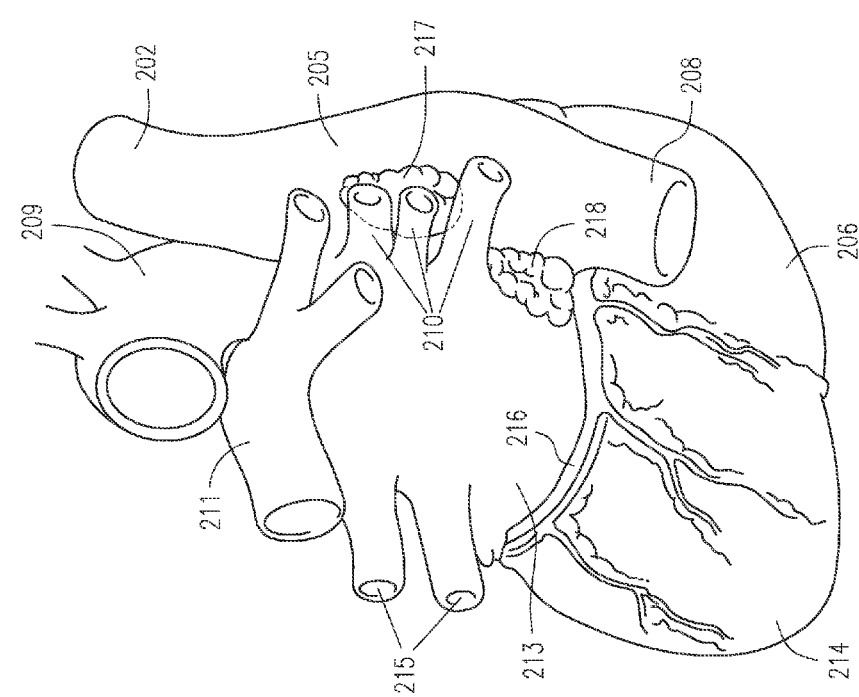

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. In various embodiments, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreceptor stimulator intravascularly into the pulmonary artery.

FIGS. 2B-2C illustrate the right side and left side of the heart, respectively, and further illustrate cardiac fat pads which have ganglia or nerve endings that function as baroreceptor sites. FIG. 2B illustrates the right atrium 205, right ventricle 206, sinoatrial node 207, superior vena cava 202, inferior vena cava 208, aorta 209, right pulmonary veins 210, and right pulmonary artery 211. FIG. 2B also illustrates a cardiac fat pad 212 between the superior vena cava and aorta. Baroreceptor nerve endings in the cardiac fat pad 212 are stimulated in some embodiments using an electrode screwed or otherwise inserted into the fat pad, and are stimulated in some embodiments using an intravenously-fed lead proximately positioned to the fat pad in a vessel such as the right pulmonary artery or superior vena cava, for example. FIG. 2C illustrates the left atrium 213, left ventricle 214, right atrium 205, right ventricle 206, superior vena cava 202, inferior vena cava 208, aorta 209, right pulmonary veins 210, left pulmonary vein 215, right pulmonary artery 211, and coronary sinus 216. FIG. 2C also illustrates a cardiac fat pad 217 located proximate to the right cardiac veins and a cardiac fat pad 218 located proximate to the inferior vena cava and left atrium. Baroreceptor nerve endings in the fat pad 217 are stimulated in some embodiments using an electrode screwed or otherwise inserted into the fat pad 217, and are stimulated in some embodiments using an intravenously-fed lead proximately positioned to the fat pad in a vessel such as the right pulmonary artery 211 or right pulmonary vein 210, for example. Baroreceptors in the cardiac fat pad 218 are stimulated in some embodiments using an electrode screwed or otherwise inserted into the fat pad, and are stimulated in some embodiments using an intravenously-fed lead proximately positioned to the fat pad in a vessel such as the inferior vena cava 208 or coronary sinus or a lead in the left atrium 213, for example.

Figure 3:
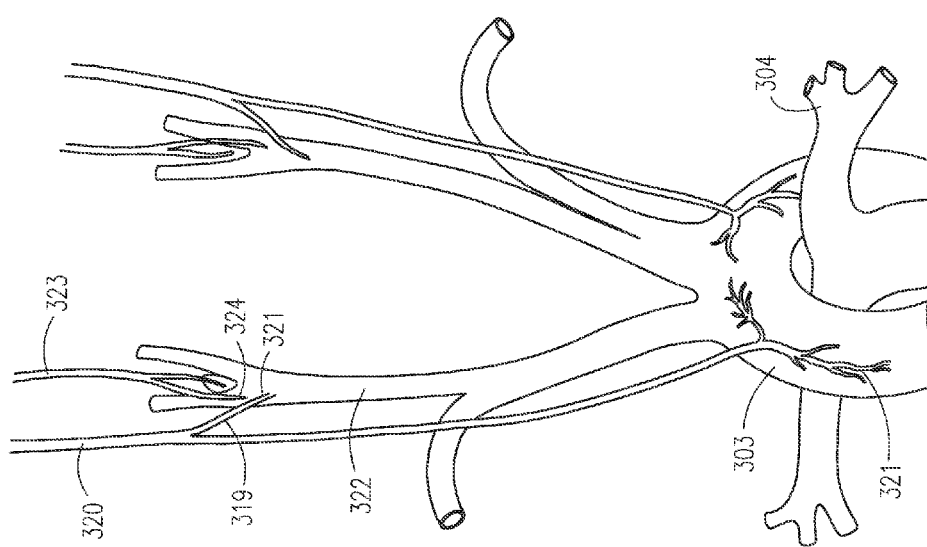
FIG. 3 illustrates baroreceptors in the area of the carotid sinus, aortic arch and pulmonary artery.

FIG. 3 illustrates baroreceptors in the area of the carotid sinus 319, aortic arch 303 and pulmonary artery 304. The aortic arch 303 and pulmonary artery 304 were previously illustrated at 203 and 204 with respect to the heart in FIG. 2A. As illustrated in FIG. 3, the vagus nerve 320 extends and provides sensory nerve endings 321 that function as baroreceptors in the aortic arch 303, in the carotid sinus 319 and in the common carotid artery 322. The glossopharyngeal nerve 323 provides nerve endings 324 that function as baroreceptors in the carotid sinus 319. These nerve endings 321 and 324, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
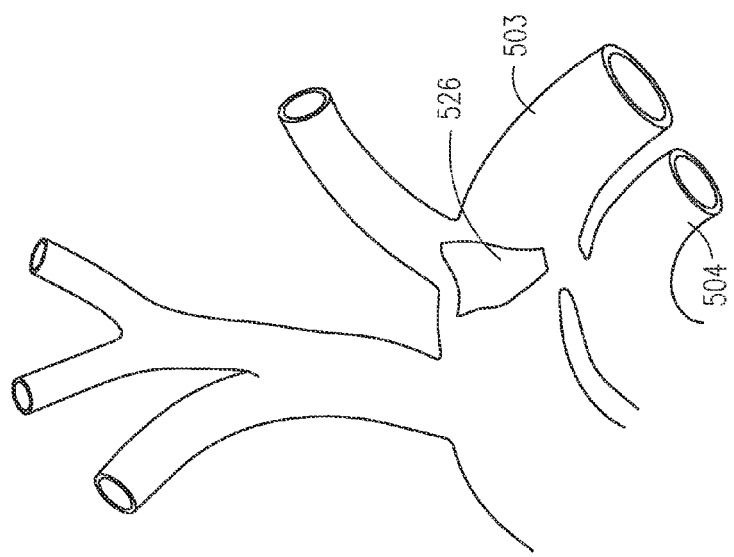
FIG. 5 illustrates baroreceptor fields in the aortic arch, near the ligamentum arteriosum and the trunk of the pulmonary artery.
Figure 4:
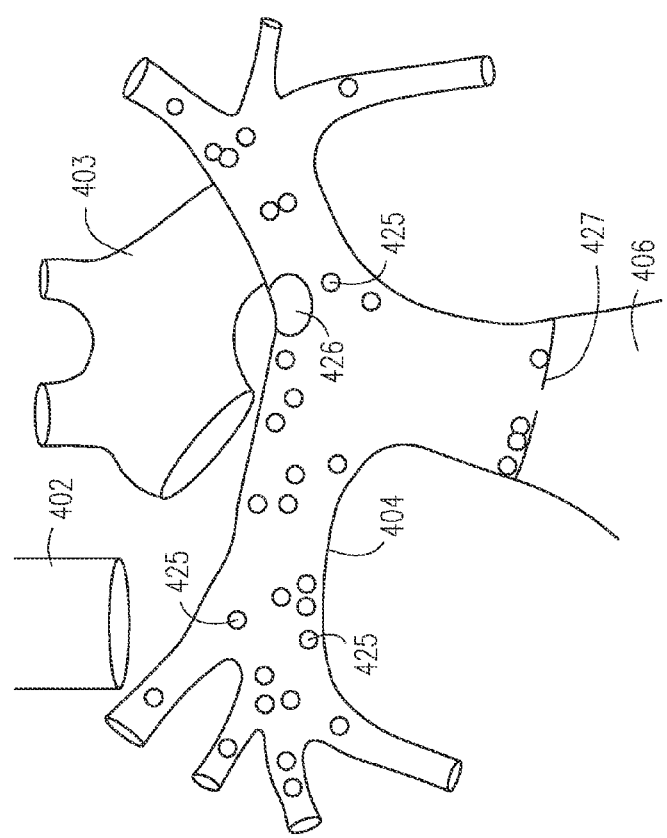
FIG. 4 illustrates baroreceptors in and around a pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 425. Furthermore, a cluster of closely spaced baroreceptors 426 is situated near the attachment of the ligamentum arteriosum. FIG. 4 also illustrates the right ventricle 406 of the heart, and the pulmonary valve 427 separating the right ventricle 406 from the pulmonary artery 404. According to various embodiments of the present subject matter, a lead is inserted through a peripheral vein and threaded through the tricuspid valve into the right ventricle, and from the right ventricle 406 through the pulmonary valve 427 and into the pulmonary artery 404 to stimulate baroreceptors and/or around the pulmonary artery. In various embodiments, for example, the lead is positioned to stimulate the cluster of baroreceptors 426 near the ligamentum arteriosum FIG. 5 illustrates baroreceptor fields 526 in the aortic arch 503, near the ligamentum arteriosum and the trunk of the pulmonary artery 504. Some embodiments position the lead in the pulmonary artery to stimulate baroreceptor sites in the aorta and/or fat pads, such as are illustrated in FIGS. 2B-2C.

Systems to Provide Neural Stimulation with Avoidance of Inappropriate Stimulation Various embodiments of the present subject matter include stand-alone implantable neural stimulator (NS) systems, include implantable devices that have integrated NS and cardiac rhythm management (CRM) components, and include systems with at least one implantable NS device and an implantable CRM device capable of communicating with each other either wirelessly or through a wire lead connecting the implantable devices. Examples of neural stimulators include anti-hypertension (AHT) devices or AHT components that are used to treat hypertension. Examples of implantable cardiac rhythm management (CRM) devices include pacemakers, implantable cardiac defibrillators (ICDs), and implantable devices capable of performing pacing and defibrillating functions. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Although implantable systems are illustrated and discussed, various aspects and embodiments of the present subject matter can be implemented in external devices. Integrating NS and CRM functions that are either performed in the same or separate devices improves aspects of the NS therapy and cardiac therapy by allowing these therapies to work together intelligently.

Figure 6:
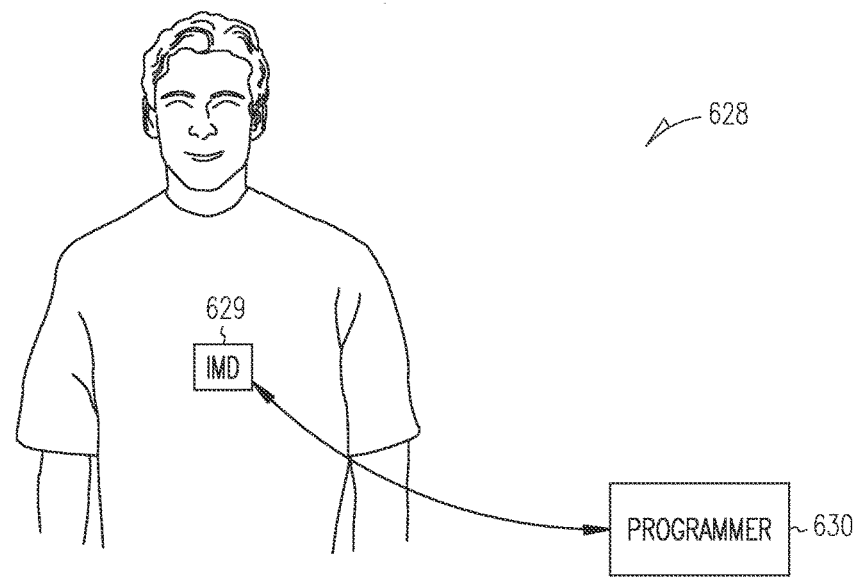
FIG. 6 illustrates a system including an implantable medical device (IMD) and a programmer, according to various embodiments of the present subject matter.

FIG. 6 illustrates a system 628 including an implantable medical device (IMD) 629 and a programmer 630, according to various embodiments of the present subject matter. Various embodiments of the IMD 629 include neural stimulator functions only, and various embodiments include a combination of NS and CRM functions. The programmer 630 and the IMD 629 are capable of wirelessly communicating data and instructions. In various embodiments, for example, the programmer 630 and IMD 629 use telemetry coils to wirelessly communicate data and instructions. Thus, the programmer can be used to adjust the programmed therapy provided by the IMD 629, and the IMD can report device data (such as battery and lead resistance) and therapy data (such as messages and sense and stimulation data) to the programmer using radio telemetry, for example.

Figure 7:
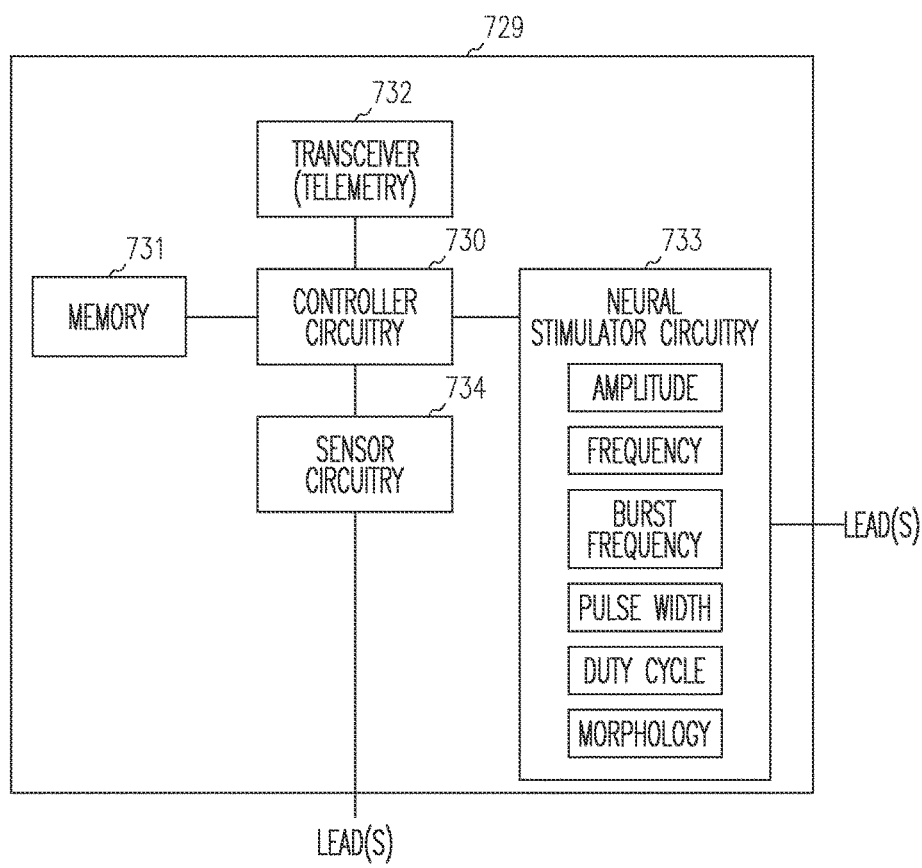
FIG. 7 illustrates an implantable medical device (IMD) such as the IMD shown in the system of FIG. 6, according to various embodiments of the present subject matter.

FIG. 7 illustrates an implantable medical device (IMD) 729 such as the IMD 629 shown in the system of FIG. 6, according to various embodiments of the present subject matter. The illustrated IMD 729 performs NS functions, and includes controller circuitry 730 and a memory 731. The controller circuitry 730 is capable of being implemented using hardware, software, and combinations of hardware and software. For example, according to various embodiments, the controller circuitry 730 includes a processor to perform instructions embedded in the memory 731 to perform functions associated with NS therapy such as AHT therapy. For example, the illustrated device 729 further includes a transceiver 732 and associated circuitry for use to communicate with a programmer or another external or internal device. Various embodiments have wireless communication capabilities. For example, some transceiver embodiments use a telemetry coil to wire communicate with a programmer or another external or internal device.

The illustrated device 729 further includes neural stimulation circuitry 733. Various embodiments of the device also includes sensor circuitry 734 used to monitor physiology parameters such as heart rate, for example. One or more leads are able to be connected to the sensor circuitry and neural stimulation circuitry. The neural stimulation circuitry is used to apply electrical stimulation pulses to desired target nerve(s), such as baroreceptor sites in the pulmonary artery, through one or more stimulation electrodes. The sensor circuitry is used to detect undesired responses, and in some embodiments insure desired responses, of the neural stimulation. Some embodiments provide sensor circuitry to detect myocardial capture, some embodiments provide sensor circuitry to detect capture of smooth muscle, and some embodiments provide sensor circuitry to detect neural activity in an non-targeted nerve. In some embodiments, the sensor circuitry is used to detect and process ANS nerve activity and/or surrogate parameters such as heart rate, blood pressure, respiration and the like, to determine the ANS activity.

According to various embodiments, the stimulation circuitry includes modules to set any one or any combination of two or more of the following pulse features: the amplitude of the stimulation pulse, the frequency of the stimulation pulse, the burst frequency, pulse width and duty cycle of a stimulation pulse, and the wave morphology of the pulse. Examples of wave morphology include a square wave, triangle wave, sinusoidal wave, and waves with desired harmonic components to mimic white noise such as is indicative of naturally-occurring baroreflex stimulation.

Figure 8:
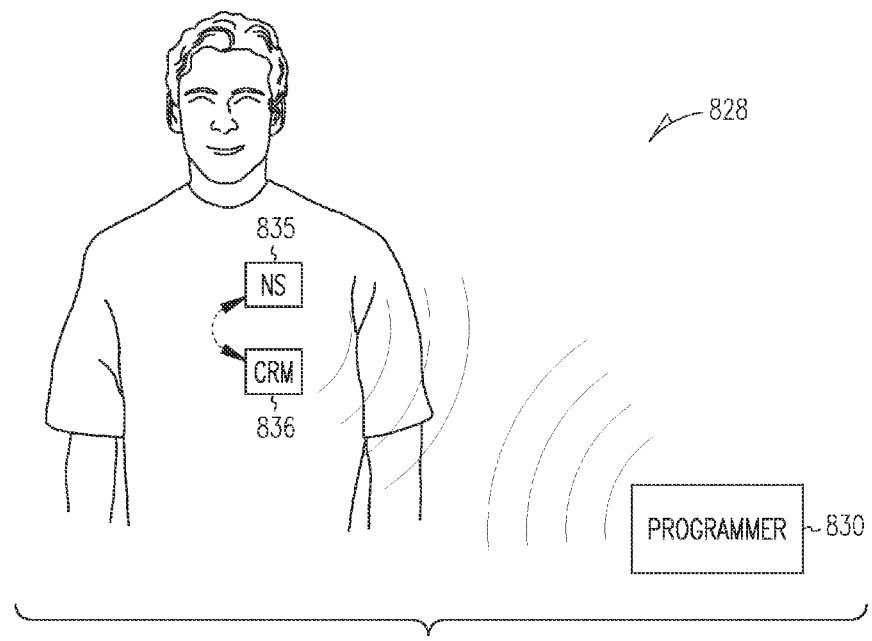
FIG. 8 illustrates a system including a programmer, an implantable neural stimulator (NS) device and an implantable cardiac rhythm management (CRM) device, according to various embodiments of the present subject matter.

FIG. 8 illustrates a system 828 including a programmer 830, an implantable neural stimulator (NS) device 835 and an implantable cardiac rhythm management (CRM) device 836, according to various embodiments of the present subject matter. Various aspects involve a method for communicating between an NS device and a CRM device or other cardiac stimulator. In various embodiments, this communication allows one of the devices 835 or 836 to deliver more appropriate therapy (i.e. more appropriate NS therapy or CRM therapy) based on data received from the other device. Thus, for example, the CRM device can detect myocardial capture by a neural stimulation pulse. Some embodiments provide on-demand communications. In various embodiments, this communication allows each of the devices 835 and 836 to deliver more appropriate therapy (i.e. more appropriate NS therapy and CRM therapy) based on data received from the other device. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means.

In some embodiments, the NS device stimulates the baroreflex to provide NS therapy, and some device embodiments sense ANS activity directly or using surrogate parameters, such as respiration and blood pressure, indicative of ANS activity. The CRM device includes cardiac stimulation capabilities, such as pacing and defibrillating capabilities. Rather than providing wireless communication between the NS and CRM devices, various embodiments provide a communication cable or wire, such as an intravenously-fed lead, for use to communicate between the NS device and the CRM device.

Figure 9:
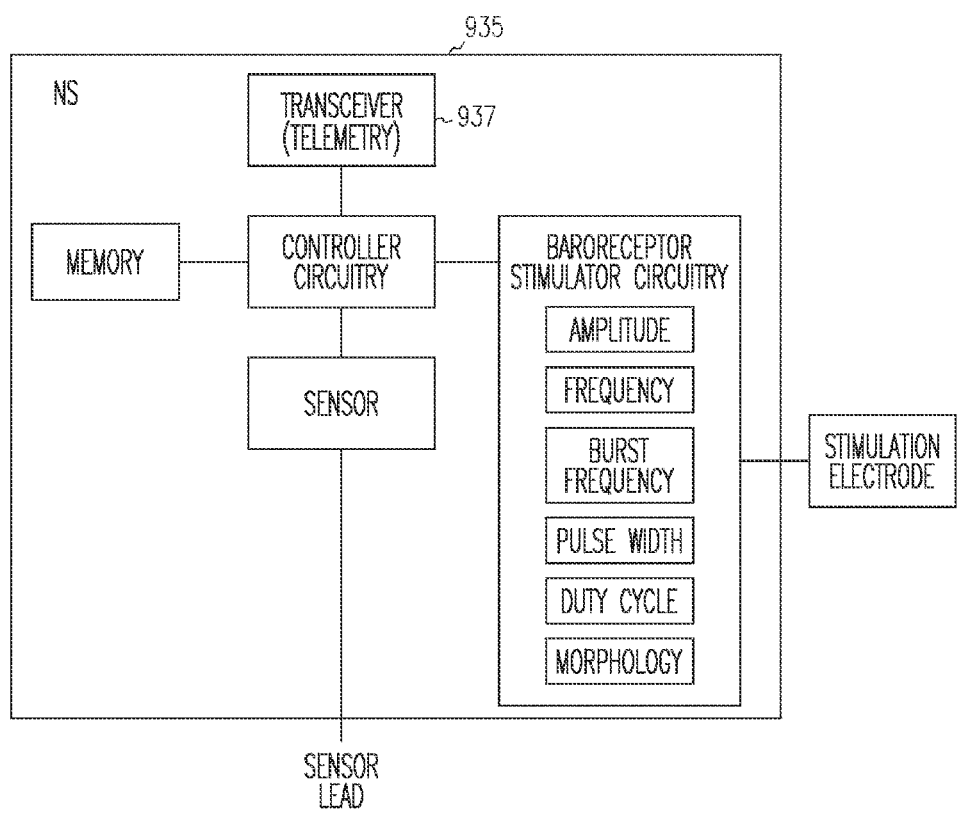
FIG. 9 illustrates an implantable neural stimulator (NS) device such as shown in the system of FIG. 8, according to various embodiments of the present subject matter.
Figure 10:
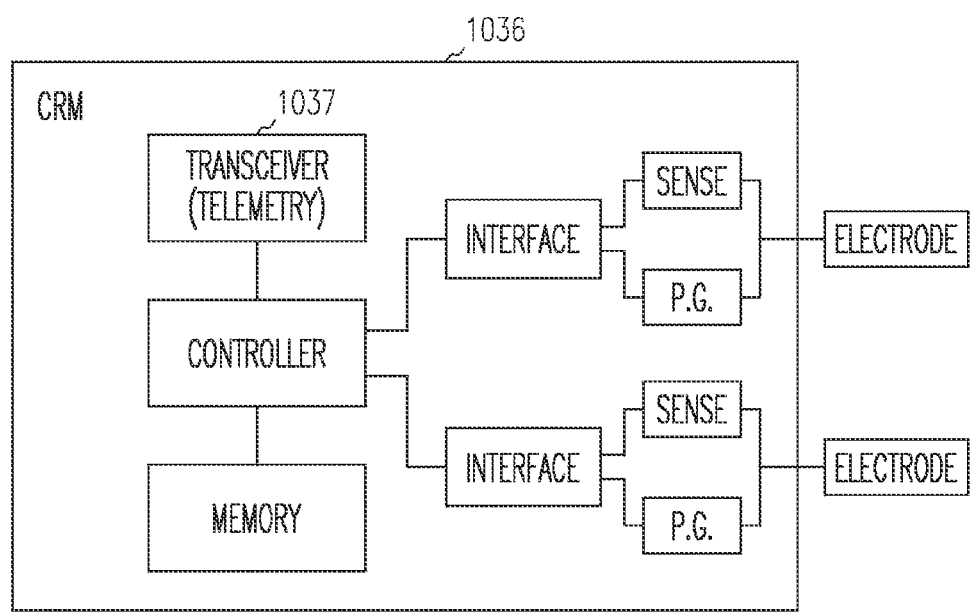
FIG. 10 illustrates an implantable cardiac rhythm management (CRM) device such as shown in the system of FIG. 8, according to various embodiments of the present subject matter.

FIG. 9 illustrates an implantable neural stimulator (NS) device 935 such as shown at 835 in the system of FIG. 8, according to various embodiments of the present subject matter. FIG. 10 illustrates an implantable cardiac rhythm management (CRM) device 1036 such as shown at 836 in the system of FIG. 8, according to various embodiments of the present subject matter. Various embodiments of the NS and CRM devices include wireless transceivers 937 and 1037, respectively, to wirelessly communicate with each other. Various embodiments of the NS and CRM devices include a telemetry coil or ultrasonic transducer to wirelessly communicate with each other.

According to various embodiments, for example, the NS device is equipped with a telemetry coil, allowing data to be exchanged between it and the CRM device, allowing the NS device to modify therapy based on electrophysiological parameters such as heart rate, minute ventilation, atrial activation, ventricular activation, and cardiac events. In addition, some CRM device embodiments modify therapy based on data received from the NS device.

Some NS device embodiments are able to be implanted in patients with existing CRM devices, such that the functionality of the NS device is enhanced by receiving physiological data that is acquired by the CRM device. For example, the CRM device is capable of detecting myocardial capture in response to the neural stimulation signal. The functionality of two or more implanted devices is enhanced by providing communication capabilities between or among the implanted devices. In various embodiments, the functionality is further enhanced by designing the devices to wirelessly communicate with each other.

Figure 11:
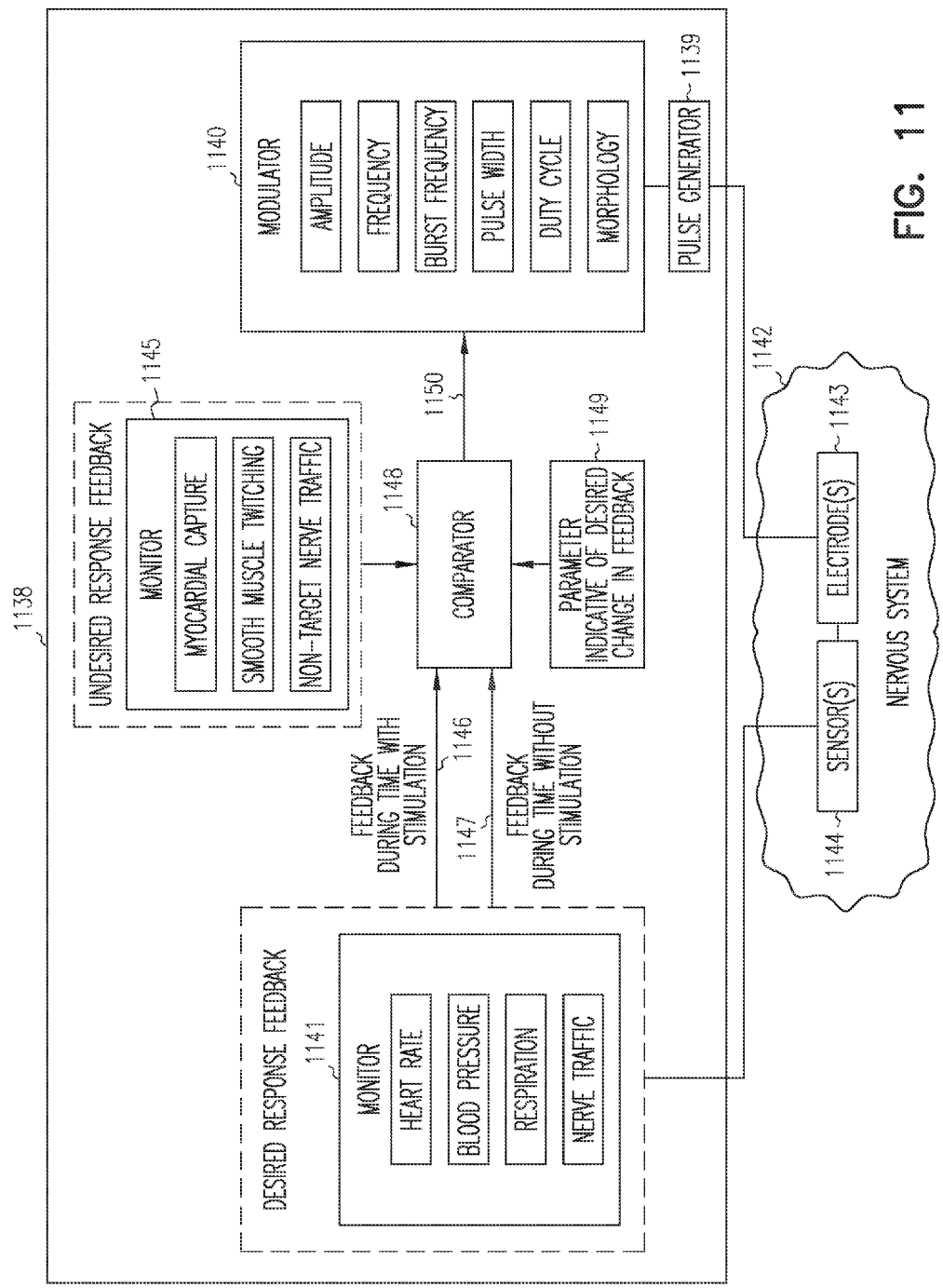
FIG. 11 illustrates a system to automatically adjust a neural stimulation signal to achieve a desired result and avoid an undesired result, according to various embodiments.

FIG. 11 illustrates a system to automatically adjust a neural stimulation signal to achieve a desired result and avoid an undesired result, according to various embodiments. The illustrated neural stimulator 1138 includes a pulse generator 1139 to provide a neural stimulation signal as part of a neural stimulation therapy, a modulator 1140 to change or modulate parameter(s) of the neural stimulation signal, and a desired response feedback monitor 1141 to provide a desired response feedback. Various stimulator embodiments are implantable. The nervous system is generally illustrated at 1142. The device 1138 uses appropriate electrode(s) 1143 to provide desired neural stimulation and sensor(s) 1144 to sense a parameter that is quickly affected by the neural stimulation. Examples of such parameters include heart rate, blood pressure, and respiration. Other parameter(s) and other surrogate parameters that have a quick and predictable response indicative of the overall response of the parasympathetic nervous system to the neural stimulation. The sensor(s) and electrode(s) can be integrated on a single lead or can use multiple leads. Additionally, various system embodiments implement the functions illustrated in FIG. 11 using an implantable neural stimulator capable of communicating with a distinct or integrated implantable cardiac rhythm management device. The illustrated device 1138 also includes an undesired response feedback monitor 1145 to provide an undesired response feedback.

The illustrated undesired response feedback monitor 1145 includes means for sensing or otherwise detecting an undesired result of the neural stimulation therapy. Various embodiments monitor cardiac activity for myocardial capture, various embodiments monitor a smooth muscle contraction for capture of the smooth muscle, and various embodiments monitor neural activity of a non-targeted nerve or a surrogate parameter associated with the non-targeted nerve. The illustrated desired feedback monitor 1141 monitors the parameter during a time with stimulation (or immediately after stimulation) to provide a first feedback signal 1146 indicative of a parameter value corresponding to a time with stimulation and during a time without stimulation to provide a second feedback signal 1147 indicative of a parameter value corresponding to a time without stimulation. The signals 1146 and 1147 are illustrated as separate lines. These signals can be sent over different signal paths or over the same signal path. A comparator 1148 receives the first and second feedback signals 1146 and 1147 and determines a detected change in the parameter value based on these signals. Additionally, the comparator compares the detected change with a desired change, as generally represented at 1149. In various embodiments, the desired change is a programmable parameter. Various embodiments program the desired change as a percent change (e.g. 5% to 10% reduction in heart rate from a heart rate during a time without stimulation to a heart rate during a time with stimulation). Various embodiments the desired change as a change in quantitative value (e.g. 5 bpm to 10 bpm reduction in heart rate from a heart rate during a time without stimulation to a heart rate during a time with stimulation). A comparison of the detected change (based on signals 1146 and 1147) and the desired change (based on value 1149) provide a comparison result 1150, which is used to appropriately control the modulator to adjust the applied neural stimulation. Various modulator embodiments change an amplitude of a stimulation signal used to provide the neural stimulation. Various modulator embodiments change a frequency of a stimulation signal used to provide the neural stimulation. Various modulator embodiments change a burst frequency of a stimulation signal used to provide the neural stimulation. Various modulator embodiments change a pulse width of a stimulation signal used to provide the neural stimulation. Various modulator embodiments change a duty cycle of a stimulation signal used to provide the neural stimulation. Various modulator embodiments change a morphology cycle of a stimulation signal used to provide the neural stimulation. Morphology examples includes sinusoidal, square, triangular and "white noise" with harmonic components that provide a signal that mimics neural activity. Various modulator embodiments change various combinations of two or more of these stimulation signal characteristics.

The illustrated system is useful in extended therapy applications. Examples of extended therapy applications involve applying stimulation to prevent remodeling of cardiac tissue and to reverse remodel cardiac tissue in cardiovascular disease. However, the present subject matter applies to other extended therapies. Neural stimulation in one of these therapies can be applied for a portion (5 to 10 seconds) of each minute, for example. Over the course of days, weeks, months and years, the efficacy of a given neural stimulation with respect to a desired response of a parasympathetic nervous system can vary for a number of reasons, such as nerve adaptation, tissue encapsulation, fibrosis, impedance changes, and the like. Additionally, systemic adaptation (i.e. an adaptation that results in attenuation of the heart rate effect in the absence of changes in the electrode or nerve) can adversely affect the efficacy of a given neural stimulation over time. The illustrated system monitors a parameter that has a quick and predictable response to an applied neural stimulation, and uses the monitored parameter to appropriately change the neural stimulation signal to result in a desired stimulation of the parasympathetic nervous system.

Programmed Therapy Applications

The devices and systems illustrated above perform neural stimulation therapy applications/processes. These processes can be performed by a processor executing computer-readable instructions embedded in memory, for example. These therapies include a number of applications, which have various processes and functions, some of which are identified and discussed below. Embodiments of a neural stimulation application include avoidance of undesired results from a neural stimulation therapy; and embodiments of a neural stimulation application include both avoidance of undesired results from a neural stimulation therapy, and insurance of a desired result from the neural stimulation therapy. The processes and functions of these therapies are not necessarily mutually exclusive, as some embodiments of the present subject matter include combinations of two or more of the below-identified processes and functions. Some features of these process are illustrated by functional blocks in the systems described and illustrated previously.

Figure 12:
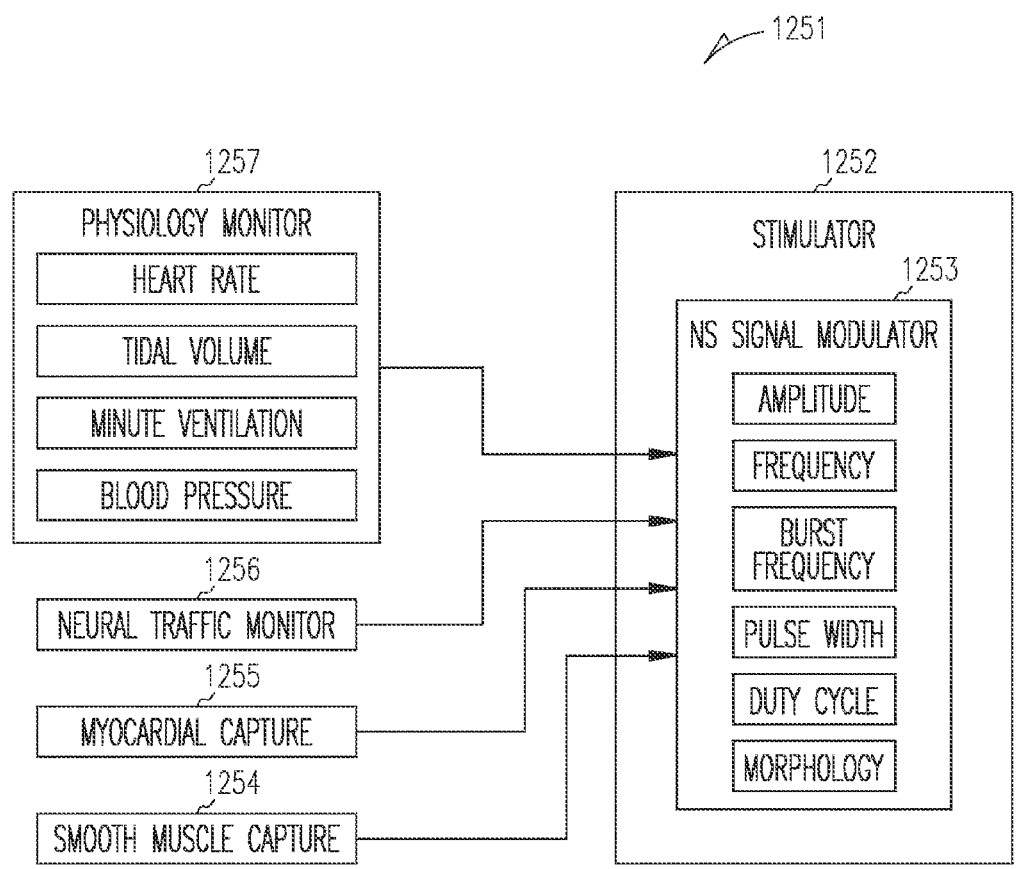
FIG. 12 illustrates an application, illustrated as functional block diagrams for a system, to modulate neural stimulation, according to various embodiments of the present subject matter.

FIG. 12 illustrates an application 1251, illustrated as functional block diagrams for a system, to modulate neural stimulation, according to various embodiments of the present subject matter. The illustrated system includes a neural stimulator 1252, such as stimulator to stimulate baroreceptors in and around the pulmonary artery. The baroreflex stimulator can be included in a stand-alone NS device or as a NS component in an integrated NS/CRM device, for example. The illustrated stimulator 1252 includes a modulator 1253 for use to selectively increase and decrease the applied neural stimulation. According to various embodiments, the modulator includes any one of the following modules: a module to change the amplitude of the stimulation pulse; a module to change the frequency of the stimulation pulse; a module to change the burst frequency of the stimulation pulse, a module to change the duty cycle of the stimulation pulse, and a module to change the morphology of the stimulation signal. According to various embodiments, the modulator includes functions for the various combinations of two or more of the modules.

The stimulation can be applied to an afferent nerve trunk such as the vagal nerve using a cuff electrode or an intravascularly-fed lead positioned proximate to the nerve trunk. The stimulation can be applied to baroreceptor sites such are located in the pulmonary artery, aortic arch, and carotid sinus, for example, using intravenously-fed leads. The stimulation can be applied to baroreceptor sites located in cardiac fat pads using intravenously-fed leads or by screwing electrodes into the fat pads.

Embodiments include one or more monitors to detect an undesired result, and in some embodiments, a desired result along with an undesired result. Undesired results include myocardial capture 1254, capture of smooth muscle 1255, and depolarization of a non-targeted nerve, which can be detected by a neural traffic monitor 1256 and/or a physiology monitor 1257 to detect heart rate, tidal volume, minute ventilation and/or blood pressure. The modulator 1253 is responsive to at least one of the monitors 1254, 1255, 1256 and 1257 to appropriately adjust parameter(s) of the neural stimulation signal to avoid undesired results from inappropriate stimulation, and in some embodiments, insure desired results from stimulation of the targeted nerve(s).

Figure 13:
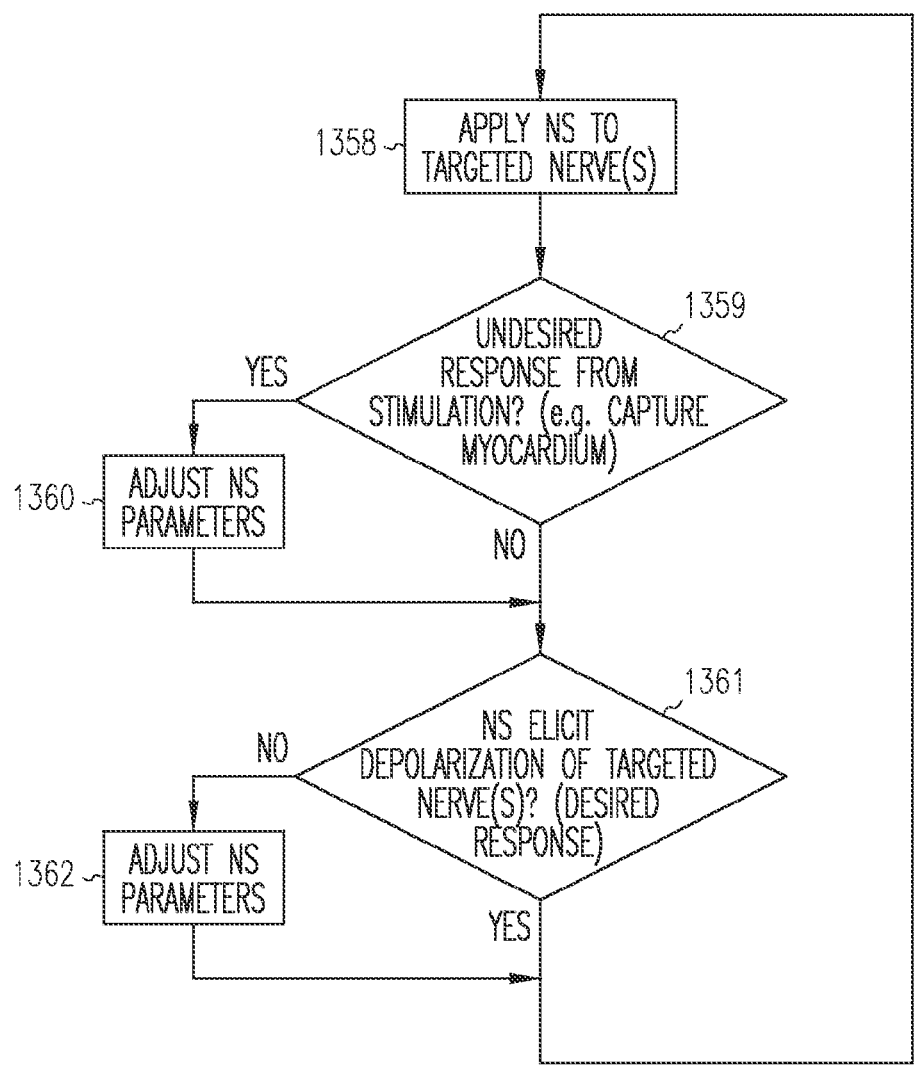
FIG. 13 illustrates a neural stimulation application, according to various embodiments.

FIG. 13 illustrates a neural stimulation application, according to various embodiments. At 1358, neural stimulation is applied to targeted nerve(s). At 1359, it is determined whether the neural stimulation results in an undesired response. For example, one embodiment determines whether the neural stimulation results in an undesired myocardial capture. If the neural stimulation results in an undesired response, at least one neural stimulator parameter is adjusted at 1360. If the neural stimulation does not result in a desired response, some embodiments determine, at 1361, whether the neural stimulation provides a desired response by depolarization of targeted nerve(s). If the neural stimulation does not depolarize the targeted nerve(s), at least one neural stimulator parameter is adjusted at 1362. Other embodiments perform the illustrated functions in a different order.

Figure 14:
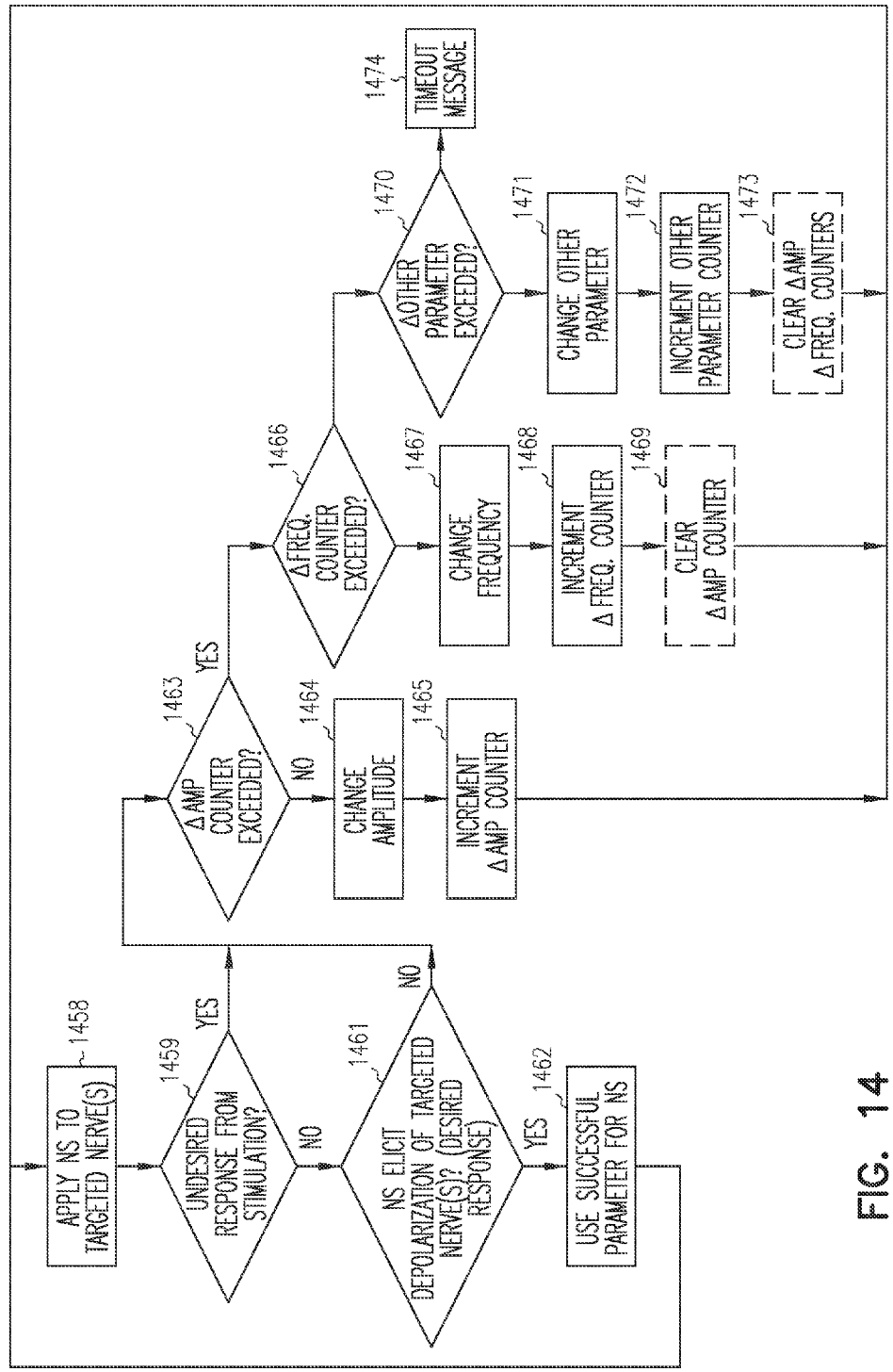
FIG. 14 illustrates a neural stimulation application, according to various embodiments.

FIG. 14 illustrates a neural stimulation application, according to various embodiments. At 1458, neural stimulation is applied to targeted nerve(s). At 1459, it is determined whether the neural stimulation results in an undesired response. For example, one embodiment determines whether the neural stimulation results in an undesired myocardial capture. If the neural stimulation does not result in a desired response, the illustrated embodiments determine, at 1461, whether the neural stimulation provides a desired response by eliciting depolarization of targeted nerve(s). If the neural stimulation depolarizes the targeted nerve(s), the successful neural stimulation signal parameter(s) are used to the NS therapy, as illustrated at 1462.

If an undesired response from the stimulation is detected at 1459 or a desired response from the stimulation is not detected at 1461, the process proceeds to change an amplitude of the neural stimulation signal, then change a frequency of the neural stimulation signal if the amplitude change was not effective, and then change another parameter of the neural stimulation signal if the changes to the amplitude and frequency were not effective. Thus, in the illustrated embodiment, for example, the process proceeds to 1463 to determine if an amplitude change counter is exceeded. If the counter is not exceeded, the process continues to change an amplitude (decrease if detected undesired response and increase if did not detect desired response) at 1464, increment the amplifier change counter at 1465, and continue to apply the NS therapy at 1458.

If, at 1463, it is determined that that the amplitude change count is exceeded, the process proceeds to determine if a frequency change counter is exceeded at 1466. If the counter is not exceeded, the frequency is changed at 1467, the frequency counter is incremented at 1468, and NS therapy continues at 1458. Some embodiments clear the amplifier change counter at 1469, such that the amplitude will be changed again for the new frequency before changing the frequency again.

If at 1466, it is determined that the frequency change count is exceeded, the process proceeds to 1470 to determine if an other signal parameter change is exceeded. If the counter is not exceeded, the parameter is changed at 1471, the other parameter counter is incremented at 1472, and NS therapy continues at 1458. Some embodiments clear the amplitude and/or frequency counters at 1473 to modulate the amplitude and/or frequency again before modulating the other parameter. If, at 1470, the other signal parameter change counter is exceeded, a timeout message 1474 is provided. In response to a timeout message, the position of the neural stimulation leads can be adjusted. The process can continue to modulate other parameters. Examples of other parameters include pulse width, burst frequency, duty cycle and morphology.

Figure 15:
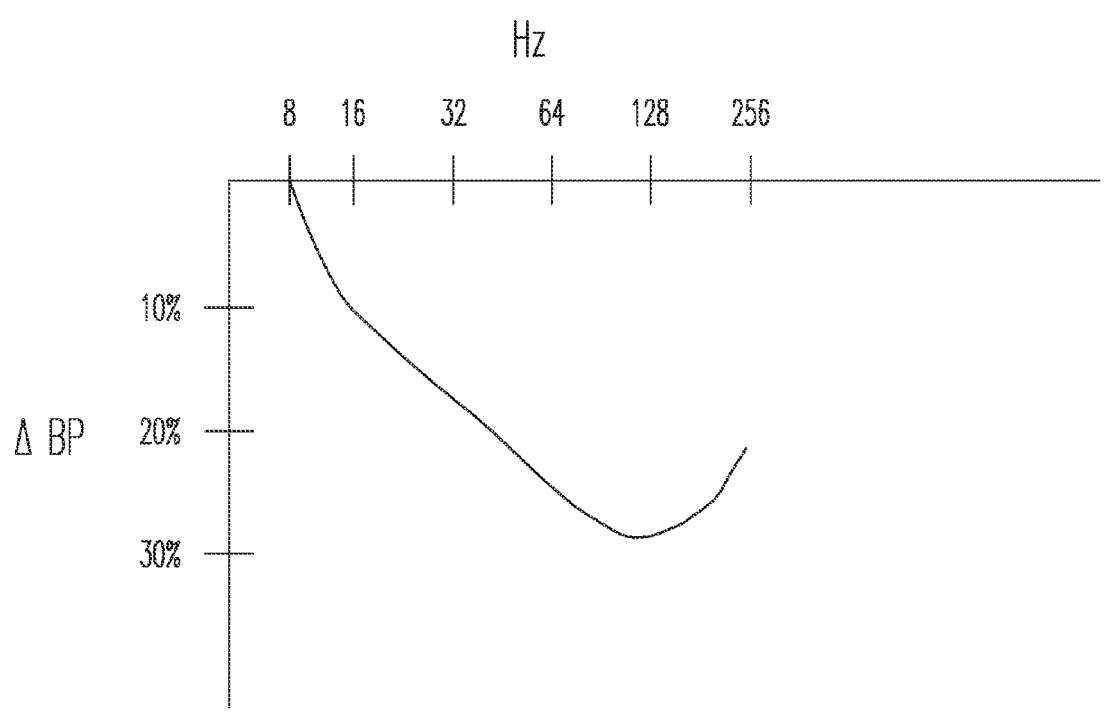
FIG. 15 is a graphical illustration of the relationship between a change in blood pressure and a rate of a stimulation signal.

FIG. 15 is a graphical illustration of the relationship between a change in blood pressure and a rate of a stimulation signal. The figure illustrates that the frequency of the stimulation signal significantly affects the decrease in blood pressure, which is a surrogate baroreflex parameter indicating the inhibition of SNA. Thus, the figure illustrates that the intensity of the neural stimulation depends on the frequency of the neural stimulation figure. The figure illustrates that a maximum decrease in blood pressure occurs at a stimulation frequency within a range from about 64 to about 256 Hz, and occurs approximately at 128 Hz.

Various embodiments of the present subject matter modulate the frequency of the stimulation signal. Various embodiments stimulate with a frequency between approximately 8 Hz and approximately 512 Hz, or various ranges within this range such as approximately 16 Hz to approximately 128 Hz, approximately 32 Hz to approximately 128 Hz, for example. Various embodiments start with a predetermined frequency estimated to provide good neural stimulation, and then gradually increase and decrease the frequency from the predetermined frequency in an effort to improve the neural stimulation intensity to the targeted nerve(s).

Figure 16:
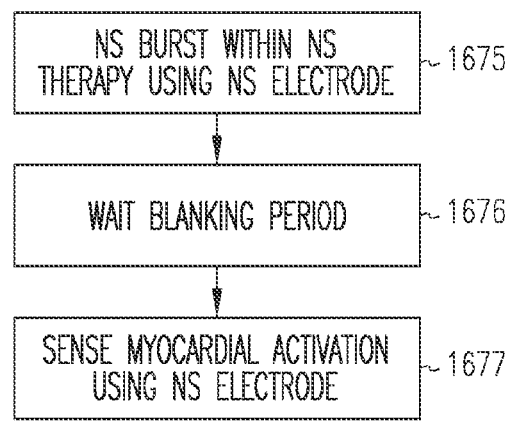
FIG. 16 illustrates a method to detect myocardial capture, according to various embodiments.

FIG. 16 illustrates a method to detect myocardial capture, according to various embodiments. Such a method can be used at 1359 and 1459 in FIGS. 13 and 14, for example. At 1675, a neural stimulation burst is applied as part of a neural stimulation therapy using a neural stimulation electrode proximate to the heart. At 1676, the device waits for a blanking period. At 1677, after the blanking period, the myocardial activation is sensed using the neural stimulation electrode.

Figure 17:
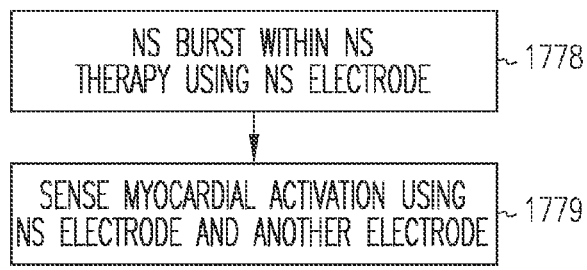
FIG. 17 illustrates a method to detect myocardial capture, according to various embodiments.

FIG. 17 illustrates a method to detect myocardial capture, according to various embodiments. Such a method can be used at 1359 and 1459 in FIGS. 13 and 14, for example. At 1778, a neural stimulation burst is applied as part of a neural stimulation therapy using a neural stimulation electrode proximate to the heart. At 1779, a myocardial activation is sensed using the neural stimulation electrode and another electrode.

Figure 18:
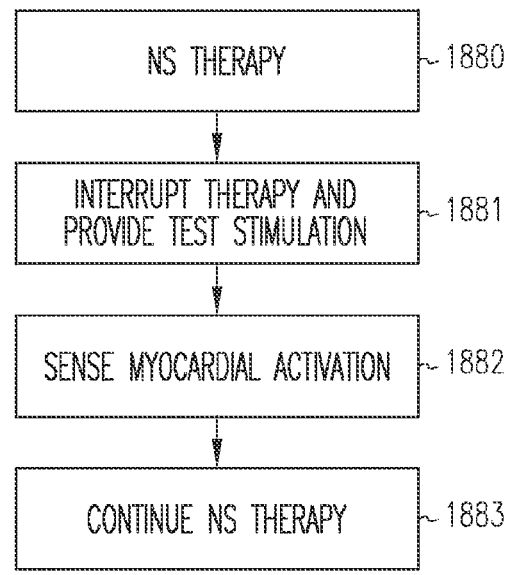
FIG. 18 illustrates a method to detect myocardial capture, according to various embodiments.

FIG. 18 illustrates a method to detect myocardial capture, according to various embodiments. Such a method can be used at 1359 and 1459 in FIGS. 13 and 14, for example. This embodiment is useful if the neural stimulation therapy includes longer stimulation bursts that depolarize the myocardium. At 1880, a neural stimulation therapy is provided. The neural stimulation therapy is interrupted at 1881 and a test stimulation burst is provided. At 1882, myocardial activation is sensed, and the neural stimulation therapy continues at 1883.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the frill scope of equivalents to which such claims are entitled.

What is claimed is:

1. An implantable device, comprising:
   a neural stimulator configured to deliver a programmed intermittent neural stimulation therapy for an extended therapy application, the programmed intermittent neural stimulation therapy including a programmed series of stimulation ON times and stimulation OFF times, each programmed stimulation ON time for the programmed intermittent neural stimulation therapy including a programmed neural stimulation burst of neural stimulation pulses, the neural stimulator including:
      a pulse generator configured to generate the neural stimulation pulses for the neural stimulation therapy; and
      a modulator to adjust the neural stimulation therapy;
   a monitor to monitor at least one physiologic response during stimulation ON times and during stimulation OFF times of the programmed intermittent neural stimulation therapy; and
   a controller operably connected to the monitor and configured to detect a change for the at least one physiologic response between the stimulation ON and stimulation OFF times and provide a therapy control signal to the modulator to achieve a desired change for the at least one physiologic response between the stimulation ON and the stimulation OFF times of the programmed intermittent neural stimulation therapy for the extended therapy application.

2. The device of claim 1, wherein the at least one physiologic response includes an undesired physiological side effect to the neural stimulation pulses, the monitor is configured to monitor for the undesired physiological side effect, and the controller is configured to provide the therapy control signal to the modulator to provide a desired no change for the monitored undesired physiological side effect.

3. The device of claim 2, wherein the undesired physiological side effect includes myocardial capture.

4. The device of claim 1, wherein the at least one physiologic response includes a change in a physiological feedback parameter intended to be affected by the neural stimulation pulses to provide feedback for the programmed intermittent neural simulation therapy, the monitor is configured to monitor for the change in the physiological feedback parameter, and the controller is configured to provide the therapy control signal to the modulator to provide a desired change for the monitored physiological feedback parameter.

5. The device of claim 4, wherein the physiological feedback parameter includes a parameter selected from the group consisting of: a sensed heart rate parameter, a sensed blood pressure parameter, a sensed respiration parameter or a sensed nerve traffic parameter.

6. The device of claim 4, wherein the controller, the neural stimulator, and monitor are configured to cooperate to generate a burst of neural stimulation pulses and deliver the burst to a neural stimulation electrode, wait a blanking period to depolarize the neural stimulation electrode, and sense for a myocardial activation using the neural stimulation electrode.

7. The device of claim 4, wherein the controller, the neural stimulator, and monitor are configured to cooperate to generate a burst of neural stimulation pulses and deliver the burst to a neural stimulation electrode, and sense for a myocardial activation using the neural stimulation electrode and another electrode.

8. The device of claim 1, wherein:
the at least one physiologic response includes an undesired physiological side effect to the neural stimulation pulses and further includes a change in a physiological feedback parameter intended to be affected by the neural stimulation pulses to provide feedback for the programmed intermittent neural simulation therapy;
the monitor is configured to monitor for the undesired physiological side effect and monitor for the change in the physiological feedback parameter; and
the controller is configured to provide the therapy control signal to the modulator to provide a desired no change for the monitored undesired physiological side effect and provide a desired change for the monitored physiological feedback parameter.

9. The device of claim 8, wherein:
the physiological feedback parameter includes a parameter selected from the group consisting of: a sensed heart rate parameter, a sensed blood pressure parameter, a sensed respiration parameter or a sensed nerve traffic parameter; and
the undesired physiological side effect to the neural stimulation pulses includes myocardial capture.

10. The device of claim 1, wherein the modulator is configured to adjust at least one of an amplitude or a frequency of the neural stimulation pulses to achieve the desired change for the at least one physiologic response between the stimulation ON and the stimulation OFF times.

11. The device of claim 10, wherein the controller is configured to adjust the amplitude of the neural stimulation pulses in an attempt to achieve the desired change for the at least one physiologic response, and adjust the frequency of the neural stimulation pulses if adjusting the amplitude alone is unable to achieve the desired change for the at least one physiologic response.

12. The device of claim 1, wherein the modulator is configured to adjust at least one of a burst frequency or a duty cycle of the neural stimulation therapy to achieve the desired change for the at least one feedback response between the stimulation ON and the stimulation OFF times.

13. The device of claim 1, wherein the modulator is configured to adjust a pulse width of the neural stimulation pulses to achieve the desired change for the at least one feedback response between the stimulation ON and the stimulation OFF times.

14. The device of claim 1, wherein the at least one physiological response includes heart rate.

15. The device of claim 1, wherein the at least one physiological response includes blood pressure.

16. The device of claim 1, wherein the at least one physiological response includes respiration.

17. The device of claim 1, wherein the at least one physiological response includes nerve traffic.

18. The device of claim 1, wherein the device is configured to stimulate a vagus nerve or a carotid sinus nerve.

19. The device of claim 1, wherein the device includes an intravascular electrode configured for placement proximate to baroreceptors in a carotid sinus or configured for placement proximate to baroreceptors in a pulmonary artery, wherein the device is configured to use the intravascular electrode to transvascularly stimulate a baroreflex response.

20. The device of claim 1, wherein the device is configured to stimulate a cardiac fat pad.

* * * * *